United States Patent [19]

Nohira et al.

[11] Patent Number: 4,978,666
[45] Date of Patent: Dec. 18, 1990

[54] OPTICALLY ACTIVE PIPERAZINE DERIVATIVE

[75] Inventors: Hiroyuki Nohira, Saitama; Mitsuo Masaki, Chiba; Masao Yamamoto, Saitama, all of Japan

[73] Assignee: Nippon Chemiphar Co., Ltd., Tokyo, Japan

[21] Appl. No.: 390,658

[22] Filed: Aug. 7, 1989

[30] Foreign Application Priority Data

Aug. 5, 1988 [JP] Japan .................. 63-196427

[51] Int. Cl.$^5$ .................. A61K 31/495; C07D 295/08
[52] U.S. Cl. ...................... 514/255; 544/396
[58] Field of Search .................. 544/396; 514/255

[56] References Cited

U.S. PATENT DOCUMENTS 3,868,377  2/1975  Raabe et al. .................. 544/396
4,528,194  7/1985  Masaki .................. 514/255

Primary Examiner—Cecilia Shen
Attorney, Agent, or Firm—McAulay Fisher Nissen & Goldberg

[57] ABSTRACT

A novel (−)-optically active piperazine derivative of the formula:

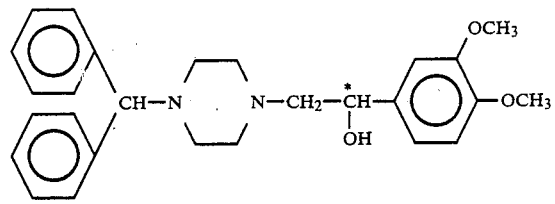

(wherein the mark of * indicates an optically active carbon) shows an increased cerebral circulation-improving effect as well as an enhanced safety.

4 Claims, 1 Drawing Sheet

OPTICALLY ACTIVE PIPERAZINE DERIVATIVE

BACKGROUND OF THE INVENTION

1. Field of Invention

This invention relates to a novel (—)-optically active piperazine derivative and a cerebral cirulationimproving agent containing the piperazine derivative as an active ingredient.

2. Description of Prior Art

U.S. Pat. No. 4,528,194 describes that piperazine derivatives of the formula:

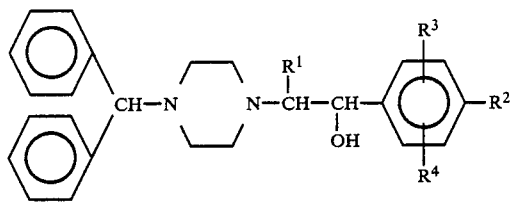

wherein $R^1$ is hydrogen or a lower alkyl group, $R^2$ is hydroxyl, an aralkyloxy group, a lower alkoxy group or a lower alkenyloxy group, $R^3$ is hydrogen, an aralkyloxy group, a lower alkoxy group, a lower alkenyloxy group, and $R^4$ is hydrogen or a lower alkoxy group and pharamceutically acceptalbe salt thereof are effective to selectively vasodilate peripheral vessels, particularly vertebrae, in increasing blood flow and suppressing platelet coagulation and therefore effectively useful as cerebral cirulation-improving agents.

SUMMARY OF THE INVENTION

The preesent inventors have discovered that (—)-optically active piperazine derivative of the formula (I):

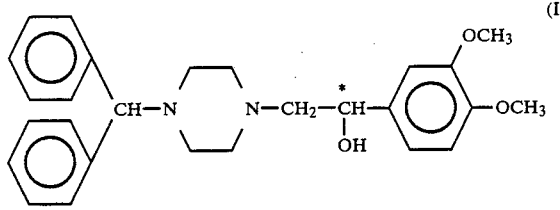

(wherein the mark of * indicates an optically active carbon) shows an increased cerebral circulation-improving effect as well as an enhanced safety, as compared with an optically unresolved piperazine derivative corresponding to the above formula (I) which is concretely described in U.S. Pat. No. 4,528,194.

DETAILED DESCRIPTION OF THE INVENTION

Figure 1:
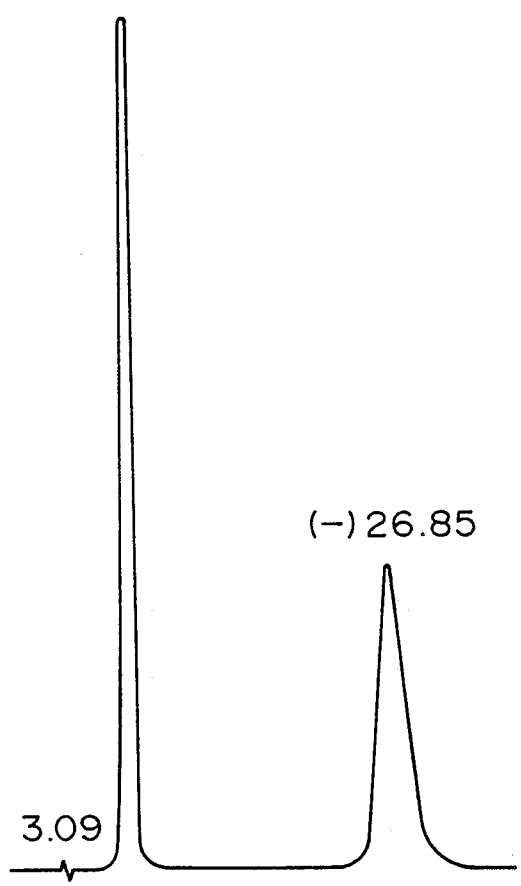
FIG. 1 shows a chromatogram obtained in high performance liquid chromatography which was conducted for optically resolving a piperazine derivative in Example 3.

The (—)-optically active piperazine derivative of the formula (I) can be prepared by optically resolving an unresolved piperazine derivative (racemic compound) corresponding to the formula (I). Such corresponding piperazine derivative in racemic form can be prepared in the manner disclosed in U.S. Pat. No. 4,528,194.

The resolution of the piperazine derivative can be performed using a resolving agent such as an acid optical resolving agent or by means of a high performance liquid chromatography.

In the process of the resolution using a resolving agent, a racemic piperazine derivative (mixture of optically active derivatives) is reacted with the resolving agent in an appropriate solvent, and thus produced two diastereomer salts are separated based on difference of solubility in the solvent. In more detail, a diastereomer salt having lower solubility is precipitated, and another diastereomer salt having higher solubility is left in the solution. The precipitated diastereomer salt is then collected, and an optically active derivative is liberated. The well soluble diastereomer salt is then collected, and another optically active derivative is liberated.

Examples of the acid optical resolving agents include tartaric acid, diacyltartaric acid, malic acid, camphor-10-sulfonic acid, mandelic acid, 3-bromocamphor-8-sulfonic acid, 3-bromocamphor-10-sulfonic acid, 8-bromocamphor-10-sulfonic acid, cis-2-benzamidocyclohexanecarboxylic acid, O-benzoylmalic acid, glutamic acid, O-methylmandelic acid, and α-methoxy-α-trifluoromethylphenylacetic acid. As tartaric acid, L-tartaric acid and D-tartaric acid both can be employed. Examples of optically active diacyltartaric acids include dibenzoyltartaric acid, di-p-toluoyltartaric acid, diacetyl tartaric acid and dipropionyltartaric acid. These diacyltartaric acids can be any of (—)-isomers and (+)-isomers. In the case that (+)-dibenzoyltartaric acid is employed as an optically active diacyltartaric acid, the (—)-optically active piperazine derivative of the invention precipitates as a sparingly soluble diastereomer, while a corresponding (+)-optically active piperazine derivative which is very soluble is left in the solution.

There is no specific limitation with respect to the ratio between the piperazine derivative and the resolving agent, but it is preferred that ¼ to 1 mole of the resolving agent is used for one mole of the optically active piperazine derivatives to be precipitated.

The reaction of the diastereomer salts with a resolving agent is generally performed in a solvent.

Examples of the solvents to be employed in the resolution process include aliphatic alcohols such as methanol, ethanol, 1-propanol, 2-propanol, 1-butanol and 2-butanol; ketones such as acetone and methyl ethyl ketone; acetonitrile; aliphatic acid esters such as ethyl acetate and butyl acetate; and ethers such as dioxane and tetrahydrofuran (THF). These solvents can be used singly or in combination of two or more kinds of solvents. Further, these solvents can be employed in combination with water. Preferred is methanol.

After the reaction is complete, the reaction mixture is cooled and left to stand at a predetermined temperature until an appropriate amount of crystals are deposited. If necessary, a solvent is supplemented, before the reaction mixture is cooled. In this procedure, the reaction mixture can be stirred, if it is advantageous. A small amount of crystals of the same salt as the diastereomer salt can be added to serve as seed crystals for accelerating precipitation of crystals. The resolving conditions (e.g., nature and composition of the solvent, concentration of the solid material, and temperature and period of time for precipitation of the crystals) for the precipitation of one stereomer salts can be determined to give the desired optically active piperazine derivative having purity as high as possible. Such resolving conditions can be easily determined by those skilled in the art.

The precipitated diastereomer salt is collected by filtration to obtain the desired diastereomer salt. If required, the diastereomer salt is can be subjected to a purification process such as partial dissolution or recrystallization using the same solvent as that employed in the resolution of the diastereomer salt.

The diastereomer salt is then treated with a base such as sodium carbonate, sodium hydroxide, potassium carbonate or potassium hydroxide to liberate the diastereomer. The liberated diastereomer can be further subjected to extraction, washing, drying and the like to give the desired (−)-optically active piperazine derivative.

The (−)-optically active piperazine derivative can be treated with an inorganic acid (e.g., hydrochloric acid, sulfuric acid, or phosphoric acid) or an organic acid (e.g., acetic acid, propionic acid, tartaric acid, malic acid, oxalic acid, or methanesulfonic acid) to give a phamaceutically acceptable acid addition salt.

As the starting material, namely, a mixture of the optically active piperazine derivatives, the piperazine derivative in its racemic form can be employed. In one embodiment of the resolution, the piperazine derivative in the racemic form can be once resolved to partly remove the undesired (+)-derivative, and the remaining mixture which is relatively rich with the (−)-derivative is further subjected to resolution to obtain the desired (−)-optically acitve piperazine derivative having high purity.

In the high performance liquid chromatography, the piperazine derivative in the racemic form or in the form of a mixture of (+)- and (−)-forms can be passed through a column of an acidic glycoprotein (e.g., $\alpha_1$-acidic glycoprotein-coated silica gel column, 4 mm I.D.×100 mm, available by the tradename of LKB Enatio Pac) using a moving phase of a phosphate-containing mixture solvent (e.g., a mixture of 8 mM sodium phosphate buffer (pH 7.5), 0.1M NaCl, 0.5 mM N,N-dimethyloctylamine, and 8% isopropanol) to obtain the desired (−)-optically active piperaine derivative. In the high performance liquid chromatography, a combination of cellulose triester or a cellulose tricarbamate derivative as the fixed phase and a mixture of hexane and 2-propanol or other solvent mixture can be employed for performing the desired resolution.

The peripheral vasodilating effect (action for increase of blood flow of vertebrae) and acute toxicity of (−)-1-(3,4-dimethoxyphenyl)-2-(4-diphenylmethyl-piperazinyl)ethanol dihydrochloride according to the invention, (+)-1-(3,4-dimethoxyphenyl)-2-(4-diphenyl-methylpiperazinyl)ethanol dihydrochloride, and (±)-1-(3,4-dimethoxyphenyl)-2-(4-diphenylmethyl-piperazinyl)ethanol dihydrochloride are illustrated by the following examples.

PERIPHERAL VASODILATING EFFECT

Mongrel Dogs of both sexes each weighing about 10 kg were anesthetized with sodium pentobarbital (35 mg/kg, i.v.). Artificial respiration was performed with room air. The vertebral blood flow and femoral blood flow were measured by an electromagnetic flowmeter (avilable from Nihon Koden, MF-27 and MFV-1100) with flow probes. The blood pressure and heart rate were measured at the same time. For intravenous administration of each compound (1 mg/kg), the cephalic vein was cannulated and a solution of the tested compound in distilled water was injected.

The dose and test results are set forth in Table 1.

TABLE 1

| Tested Compound | Dose (mg/kg, i.v.) | Percentage of vertebral blood flow increase (%) |
|---|---|---|
| (−)-Derivative | 0.1 | 48.0 |
|  | 0.03 | 22.9 |
| (+)-Derivative | 0.1 | 34.3 |
|  | 0.03 | 13.4 |
| (±)-Derivative | 0.1 | 43.9 |
|  | 0.03 | 16.9 |

As is apparent from the results shown in Table 1, the (−)-optically active piperazine derivative shows prominently high vertebral blood flow increasing action, as compared with the (+)-optically active piperazine derivative and the (±)-piperazine derivative.

Further, it has been confirmed that adminitstration of the (−)-derivative into beagle dogs shows high concentration in blood (determined from an area of a measured blood concentration curve), as compared with administration of the (+)-derivative.

ACUTE TOXICITY

Each of the (−)-, (+)- and (±)-piperazine derivatives were orally administered to SD-strain female rats each having a body weight of 150 to 200 g. The rats were observed for 2 weeks to determine their $LD_{50}$ values. The test results are set forth in Table 2.

TABLE 2

| Tested Compound | $LD_{50}$ (mg/kg) |
|---|---|
| (−)-Derivative | 45.4 |
| (+)-Derivative | 14.3 |
| (±)-Derivative | 29.1 |

It is generally accepted that one optically active compound showing a higher pharmacological action than another optically active compound having the same chemical formula has higher toxicity as another compound. Nevertheless, as is apparent from the results shown in Table 2, the (−)-optically active piperazine derivative shows prominently weak toxicity, as compared with the (+)-optically active piperazine derivative and the (±)-piperazine derivative.

As is clear from the above test results, the (−)-optically active piperazine derivative of the invention shows an increased cerebral circulation-improving action as well as high absorption, but is less in toxicity. Accordingly, the (−)-optically active piperazine derivative of the invention is very favorable for the use as a pharmaceutical.

The (−)-optically active piperazine derivative of the present invention can be administered either orally or parenterally. Preparation forms for oral administration can be, for example, tablets, capsules, powder, granules, syrup and the like. Preparation forms for parenteral administration can be injectable preparations and the suppositories. For the formulation of these preparations, excipients, disintegrants, binders, lubricants, pigments, diluents and the like which are commonly used in the art can be used. Examples of the excipients include dextrose, lactose and the like. Starch, carboxymethylcellulose calcium and the like may be used as the disintegrants. Magnesium stearate, talc and the like can be used as the lubricants. The binders can be hydroxypropylcellulose, gelatin, polyvinylpyrrolidone and the like.

The dose may usually be about 10 mg/day to 400 mg/day for an adult. The dose may be either increased or decreased depending on the age and other conditions.

Examples of the preparation of the (−)-optically active piperazine derivative of the formula (I) are given below.

EXAMPLE 1

(a) In 1,000 ml of methanol was dissolved by heating 25.95 g (60 mmol) of (±)-racemic compound of 1-(3,4-dimethoxyphenyl)-2-(4-diphenylmethylpiperazinyl)ethanol (referred to hereinafter as "derivative"). To the resulting solution was dropwise added under reflux a solution of 16.93 g (45.0 mmol) of (−)-dibenzoyltartaric acid monohydrate in 200 ml of methanol. The reflux was continued for a while. Subsequently the mixture was allowed to stand for two nights at room temperature. Crystals precipitated. The crystals were collected by filtration to give 18.21 g of a crude diastereomer of (−)-dibenzoyltartarate with the (+)-derivative.

(b) The crude diastereomer of (−)-dibenzoyltartarates with the (+)-derivative obtained in (a) above (18.11 g) was recrystallized twice from methanol to give 6.96 g of a purified dibenzoyltartarate.

$[\alpha]_D^{23} = -22.9°$ (c=0.105, methanol).

(c) The purified (−)-taratarate diastereomer of the (+)-derivative obtained in (b) above (5.62 g, 5.0 mmol) was extracted with dichloromethane, after addition of saturated aqueous sodium carbonate. The extract was washed with saturated aqueous sodium chloride and dried over anhydrous potassium carbonate. The solvent was distilled off to leave 4.00 g of crystals of the (+)-derivative.

$[\alpha]_D^{23} = +35.0°$ (c=1.57, chloroform)

(d) The crystals of the (+)-derivative (3.83 g, 8.9 mmol) obtained in (c) above was added to a mixture of 1.53 ml of acetic acid and 0.38 ml of water. Further, 2 ml of isopropyl alcohol and 1.63 ml of conc. hydrochloric acid were added to the mixture to completely dissolve the crystals in the mixture of solvents. To the resulting solution was added 30 ml of isopropyl alcohol, and the mixture was stirred overnight. Crystals precipitated. The crystals were collected by filtration. Further, another portion of crystals which were precipitated from the filtrate by addition of hexane was collected by filtration. The collected crystals were combined, washed with isopropyl alcohol and dried under reduced pressure to give 3.97 g of the (+)-derivative dehydrochloride as a white crystalline product.

$[\alpha]_D^{23} = +23.2°$ (c=1.01, methanol).

(e) The filtrate (mother liquer) obtained in the filtration of the crude diastereomer of (−)-dibenzoyltaratarate with the (+)-derivative was concentrated. The residue was extracted with dichloromethane after addition of saturated aqueous sodium carbonate. The extract was washed with saturated aqueous sodium chloride and dried over anhydrous potassium carbonate. The solvent was distilled off to give 12.90 g of crystals of the (−)-derivative and the (+)-derivative in mixture which contained an excessive amount of the former (−)-derivative. The crystals (12.89 g, 29.8 mmol) were dissolved in 500 ml of methanol under heating. To the methanol solution was dropwise added under reflux a solution of 7.04 g (18.7 mmol) of (+)-dibenzoyltartaric acid monohydrate in 100 ml of methanol. The mixture was further refluxed and allowed to stand overnight at room temperature. Crystals precipitated. The crystals were collected by filtration to give 12.98 g of a crude diastereomer of (+)-dibenzoyltartarate with the (−)-derivative.

(f) The crude (+)-dibenzoyltartarate of the (−)-derivative (12.88 g) obtained in (e) above was once recrystallized from methanol to give 8.62 g of a purified salt.

$[\alpha]_D^{23} = +19.6°$ (c=0.102, methanol).

(g) The purified (+)-dibenzoyltartarate of the (−)-derivative (5.62 g, 5.0 mmol) was extracted with dichloromethane, after addition of saturated aqueous sodium carbonate. The extract was washed with saturated aqueous sodium chloride and dried over anhydrous potassium carbonate. The solvent was distilled off to give 3.99 g of the desired (−)-derivative as a crystalline product.

$[\alpha]_D^{23} = -34.2°$ (c=1.56, chloroform).

(h) The crystals of the (−)-derivative (3.83 g, 8.9 mmol) obtained in (g) above was added to a mixture of 1.53 ml of acetic acid and 0.38 ml of water. Further, 2 ml of isopropyl alcohol and 1.63 ml of conc. hydrochloric acid were added to the mixture to completely dissolve the crystals in the mixture of solvents. To the resulting solution was added 30 ml of isopropyl alcohol, and the mixture was stirred overnight. Crystals precipitated. The crystals were collected by filtration. Further, another portion of crystals which were precipitated from the filtrate by addition of hexane was collected by filtration. The collected crystals were combined, washed with isopropyl alcohol and dried under reduced pressure to give 4.29 g of the (−)-derivative dihydrochloride as a white crystalline product.

$[\alpha]_D^{23} = -23.1°$ (c=1.01, methanol).

EXAMPLE 2

(a) In 80 ml of methanol was dissolved by heating 2595 mg (6.0 mmol) of (±)-racemic compound of 1-(3,4-dimethoxyphenyl)-2-(4-diphenylmethyl-piperazinyl)ethanol (referred to as "derivative"). To the resulting solution was dropwise added under reflux a solution of 565 mg (1.5 mmol) of (−)-dibenzoyltartaric acid monohydrate in 10 ml of methanol. The reflux was continued for a while. Subsequently the mixture was allowed to stand overnight at room temperature. Crystals precipitated. The crystals were collected by filtration to give 1435 mg of a crude diastereomer of (−)-dibenzoyltartarate with the (+)-derivative.

(b) The crude diastereomer of (−)-dibenzoyltartarates with the (+)-derivative obtained in (a) above (1328 mg) was recrystallized once from methanol to give 867 mg of a purified dibenzoyltartarate.

$[\alpha]_D^{15} = -18.4°$ (c=0.103, methanol).

(c) The purified (−)-taratarate diastereomer of the (+)-derivative obtained in (b) above (763 mg, 0.62 mmol) was extracted with dichloromethane, after addition of saturated aqueous sodium carbonate. The extract was washed with saturated aqueous sodium chloride and dried over anhydrous potassium carbonate. The solvent was distilled off to leave 537 mg of crystals of the (+)-derivative.

$[\alpha]_D^{23} = +32.0°$ (c=1.43, chloroform).

(d) The crystals of the (+)-derivative (460 mg, 1.1 mmol) obtained in (c) above was dissolved in 5 ml of acetone. Further, 0.18 ml of conc. hydrochloric acid in 3.4 ml of acetone was added to the solution. The mixture was stirred overnight at room temperature. Crystals precipitated. The crystals were collected by filtration. The collected crystals were washed with acetone and dried under reduced pressure to give 407 mg of the (+)-derivative hydrochloride as a white crystalline product.

$[\alpha]_D^{15} = +20.6°$ (c=1.02, methanol)

(e) The filtrate (mother liquer) obtained in the filtration of the crude diastereomer of (−)-dibenzoyltaratarate with the (+)-derivative and the mother liquer which remained after the recrystallization in the step (b) were combined and concentrated. The residue was extracted with dichloromethane after addition of saturated aqueous sodium carbonate. The extract was washed with saturated aqueous sodium chloride and dried over anhydrous potassium carbonate. The solvent was distilled off to give 1905 mg of crystals of the (−)-derivative and the (+)-derivative in mixture which contained an excessive amount of the former (−)-derivative. The crystals (1900 mg, 4.4 mmol) were dissolved in 60 ml of methanol under heating. To the methanol solution was dropwise added under reflux a solution of 531 mg (1.4 mmol) of (+)-dibenzoyltartaric acid monohydrate in 10 ml of methanol. The mixture was further refluxed and allowed to stand overnight at room temperature. Crystals precipitated. The crystals were collected by filtration to give 1527 mg of a crude diastereomer of (+)-dibenzoyltartarate with the (−)-derivative.

(f) The crude (+)-dibenzoyltartarate of the (−)-derivative (1418 mg) obtained in (e) above was once recrystallized from methanol to give 1009 mg of a purified salt.

$[\alpha]_D^{16} = +21.6°$ (c=0.102, methanol).

(g) The purified (+)-dibenzoyltartarate of the (−)-derivative (902 mg, 0.74 mmol) was extracted with dichloromethane, after addition of saturated aqueous sodium carbon. The extract was washed with saturated aqueous sodium chloride and dried over anhydrous potassium carbonate. The solvent was distilled off to give 632 mg of the desired (−)-derivative as a crystalline product.

$[\alpha]_D^{16} = -32.1°$ (c=1.41, chloroform)

(h) The crystals of the (−)-derivative (579 mg, 1.3 mmol) obtained in (g) above was dissolved in 5 ml of acetone. Further, 0.22 ml of conc. hydrochloric acid in 4.2 ml of acetone was added to the mixture. The mixture was stirred overnight at room temperature. Crystals precipitated. The crystals were collected by filtration. The collected crystals were washed with acetone and dried under reduced pressure to give 537 mg of the (−)-derivative dihydrochloride as a white crystalline product.

$[\alpha]_D^{15} = -20.7°$ (c=1.01, methanol)

EXAMPLE 3

The (±)-racemic compound of 1-(3,4-dimethoxyphenyl)-2-(4-diphenylmethylpiperazinyl)ethanol (referred to as "derivative") was resolved by a high performance liquid chromatography using a column of a silica gel coated with a cellulose derivative (CHIRALCEL OD, tradename available from Daicel Corp., Japan) having the following formula:

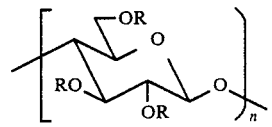

wherein R is a group having the formula:

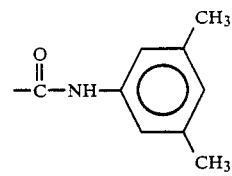

The column had a diameter of 0.46 cm and a length of 25 cm. In the chromatographic procedure, 20 mg of the derivative was dissolved in 10 ml of anhydrous ethanol and supplied in the column. The conditions of the chromatographic procedure was given below.

Moving phase (eluent): ethanol/hexane/diethylamine (80/20/0.1)
Flow rate: 1 ml/min.
Temperature of column: room temperature
Detection: Ultraviolet detection (278 nm, range 0.08)
Amount to supplied: 10 μl
Retention time of solvent: 3.09 min.
Retention time of (+)-derivative: 7.62 min.
Retention time of (−)-derivative: 26.85 min.

The chromatogram obtained in the chromatographic procedure is illustrated in the attached FIG. 1.

EXAMPLE 4

Preparation Example (Tablets)

Each tablet (220 g) contained the following components:

| Effective component | 50 mg |
|---|---|
| Lactose | 100 |
| Starch | 50 |
| Magnesium stearate | 5 |
| Hydroxypropylcellulose | 15 |

EXAMPLE 5

Preparation Example (Capsules)

Each hard gelatin capsule (350 mg) contained the following components:

| Effective component | 40 mg |
|---|---|
| Lactose | 200 |
| Starch | 70 |
| Polyvinylpyrrolidone | 5 |
| Crystalline cellulose | 35 |

EXAMPLE 6

Preparation Example (Granules)

Each granule (1 g) contained the following components:

| Effective component | 200 mg |
|---|---|
| Lactose | 450 |

-continued

| Corn starch | 300 |
|---|---|
| Hydroxypropylcellulose | 50 |

We claim:

1. A (−)-optically active piperazine compound of the formula:

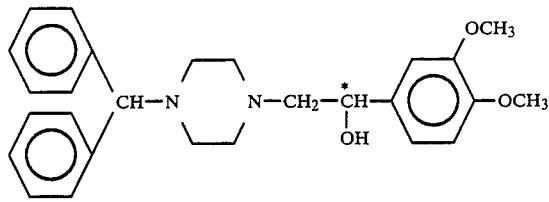

wherein the mark of * indicates an optically active carbon.

2. A cerebral circulation-improving agent containing as an active ingredient a (−)-optically active piperazine compound of the formula:

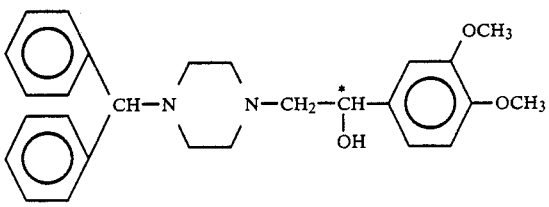

wherein the mark of * indicates an optically active carbon, or a pharmaceutically acceptable salt thereof.

3. A composition containing a cerebral circulation-improving amount of the compound of claim 1 and or a pharmaceutically acceptable salt thereof and a pharmaceutically accepted carrier therefore.

4. A method for improving cerebral circulation in mammals which comprises administering to a mammal a cerebral circulation effective amount of the compound of claim 1.

* * * * *